United States Patent

Watanabe et al.

Patent Number: 4,699,981
Date of Patent: Oct. 13, 1987

[54] CEPHALOSPORIN DERIVATIVES

[75] Inventors: Yoshiaki Watanabe, Kodaira; Chihiro Yokoo, Gyoda; Masami Goi, Saitama; Akira Onodera, Kuki; Mitsuo Murata; Hiroshi Fukushima, both of Saitama; Kaoru Sota, Tokorozawa, all of Japan

[73] Assignee: Taisho Pharmaceutical Co., Ltd., Japan

[21] Appl. No.: 893,783

[22] Filed: Aug. 6, 1986

[30] Foreign Application Priority Data

Aug. 12, 1985 [JP] Japan .................. 60-177342
Oct. 17, 1985 [JP] Japan .................. 60-231785

[51] Int. Cl.[4] ............... C07D 501/36; A61K 31/545
[52] U.S. Cl. .................. 540/227; 540/226; 514/206; 514/204
[58] Field of Search .............. 544/226, 227; 514/206

[56] References Cited

U.S. PATENT DOCUMENTS 4,097,595  6/1978  Deyms et al. ................ 540/226
4,307,116  12/1981  Page et al. .................... 540/227
4,452,851  6/1984  Takaya et al. ................ 424/246

FOREIGN PATENT DOCUMENTS 2144420  5/1985  United Kingdom.

Primary Examiner—Nicholas S. Rizzo
Attorney, Agent, or Firm—Pahl, Lorusso & Loud

[57] ABSTRACT

Cephalosporin derivatives represented by the general formula

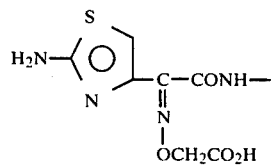

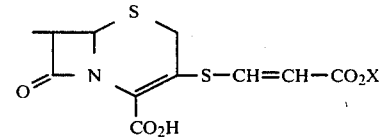

Wherein X represents a hydrogen atom, a lower alkyl group having 1 to 4 carbon atoms, an allyl group, a cycloalkyl group having 5 or 6 carbon atoms or a benzyl group, and the non-toxic salts thereof are disclosed. These compounds are useful as antibacterial agents.

5 Claims, No Drawings

CEPHALOSPORIN DERIVATIVES

The compounds of the present invention are cephalosporin derivatives represented by the general formula

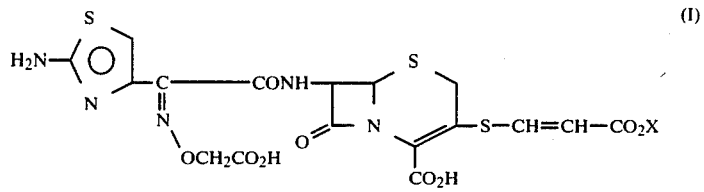

(I)

BACKGROUND OF THE INVENTION

1. Field of the Invention

The present invention relates to novel cephalosporin derivatives for oral administration, and more particularly to cephalosporin derivatives and their non-toxic salts showing excellent antibacterial effect by oral administration.

2. Description of the Prior Art

Cephalosporin drugs are widely used for the treatment and prevention of various infectious diseases caused by pathogenic bacteria.

Especially, since the cephalosporin drugs for oral administration, represented by cefalexin, can be more easily used than the one for injectional administration, they are most widely used now. Furthermore, the compounds having certain vinylthio substituents at the 3-position of cephalosporin derivative are disclosed more recently (U.K. Pat. No. 2,144,420A).

However, known cephalosporin drugs for oral administration are much inferior to the one for injectional administration in terms of antibacterial activity and antibacterial spectrum, and the problem is the remarkable increase of strains resistant to these drugs.

Under such circumstances, it is desired to find cephalosporin drugs having excellent antibacterial activity, wide antibacterial spectrum, and effective amount in the blood concentration.

SUMMARY OF THE INVENTION

As a result of the earnest studies for the purpose of finding of cephalosporin derivatives showing strong antibacterial activity, wide antibacterial spectrum and high blood concentration when administered orally, the present inventors found some cephalosporin derivatives showing antibacterial activity, antibacterial spectrum and blood concentration superior to cefalexin, and completed the present invention.

wherein X represents a hydrogen atom, a lower alkyl group having 1 to 4 carbon atoms, an allyl group, a cycloalkyl group having 5 or 6 carbon atoms or a benzyl group, and the non-toxic salts thereof.

DETAILED DESCRIPTION OF THE INVENTION

The functional groups in the present invention are as follows: the lower alkyl group having 1 to 4 carbon atoms for X refers to those which are in straight or branched chain, for example, a methyl group, an ethyl group, a n-propyl group, an isopropyl group, a n-butyl group, an isobutyl group; and the cycloalkyl group refers to a cyclopentyl group or a cyclohexyl group.

The non-toxic salts of the compound of Formula I of the invention mean those which are pharmaceutically acceptable, for example, salts with inorganic bases including sodium, potassium, calcium and mangesium; salts with organic bases such as ammonia, triethylamaine and cyclohexylamine; salts with basic amino acids such as arginine and lysine; salts with mineral acids such as sulfuric acid, hydrochloric acid and phosphoric acid; and salts with organic acids such as acetic acid, lactic acid, tartaric acid, fumaric acid, maleic acid, trifluoroacetic acid and methanesulfonic acid.

Among the preferred compounds of Formula I, are included the compounds wherein X represents a methyl group, an ethyl group, an isopropyl group or an allyl group.

The compounds of the present invention are those in the forms of geometric isomers [E-form and Z-form] derived from the oxyimino group at the 7-position side chain and the vinyl group at the 3-position side chain, respectively, and both isomers are included within the scope of the present invention, but the Z-form derived from the oxyimino group at the 7-position side chain is preferred.

The compounds of Formula I of the present invention can be, for example, obtained according to the following synthetic methods.

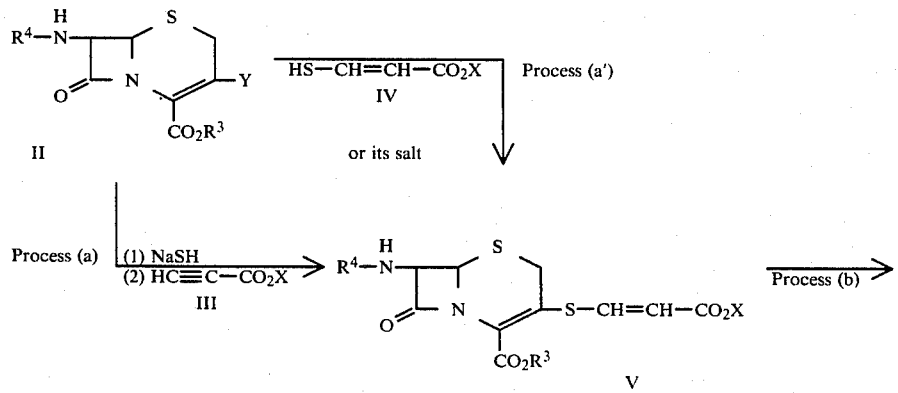

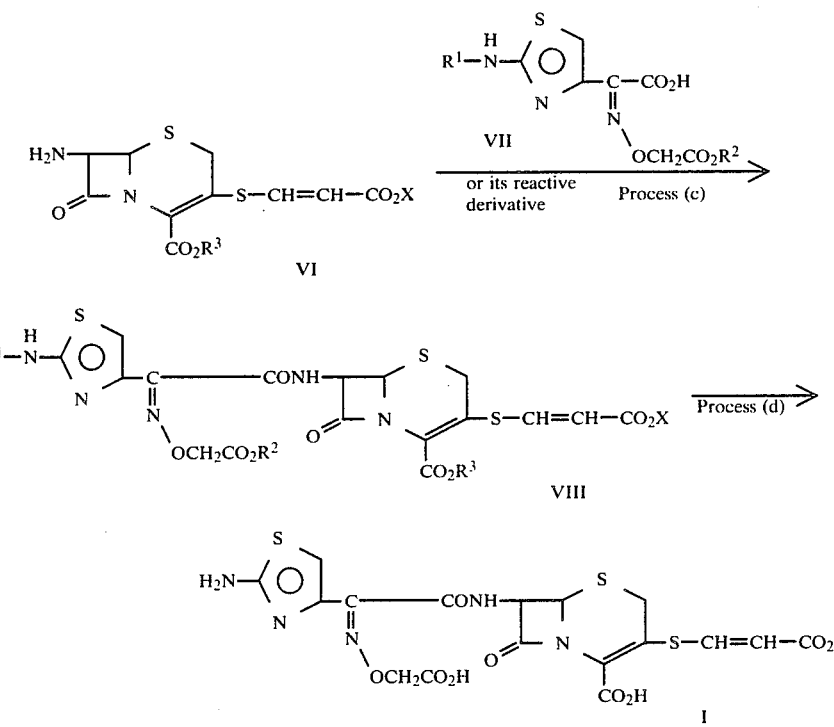

In the scheme mentioned above, X is as defined above, $R^1$ represents a protecting group of the amino group, $R^2$ and $R^3$ represent each a protecting group of the carboxyl group, $R^4$ represents a protecting group of the amino group such as a phenylacetyl group, a phenoxyacetyl group, a trityl group, a phthaloyl group, a formyl group, a benzoyl group and the like, Y represents a halogen atom (e.g., a chlorine atom, a bromine atom or an iodine atom), a methanesulfonyloxy group, a trifluomethanesulfonyloxy group, a diphenylphosphoryloxy group, a p-toluenesulfonyloxy group and the like.

The protecting groups of the amino group and carboxyl group such as $R^1$, $R^2$ and $R^3$ are those frequently used in the field of the β-lactam chemistry. For example, $R^1$ is a trityl group, a monochloroacetyl group, a formyl group, a p-methoxybenzyloxycarbonyl group and the like, $R^2$ and $R^3$ are each a benzhydryl group, a p-methoxybenzyl group, p-nitrobenzyl group, a benzyl group, a 2,2,2-trichloroethyl group, a trimethylsilyl group, an allyl group and the like.

Process (a): A known compound of Formula II is dissolved in a reaction-inert organic solvent, and reacted with 1.0 to 1.2 molar equivalents of sodium hydrosulfide in the presence of a base. The reaction temperature is from −50° C. to 100° C., preferably from −25° C. to 5° C. The reaction time is from 10 minutes to 4 hours, preferably from 10 minutes to one hour. The resulting compound, in the same reaction system (or after isolation) is reacted with 1.0 to 2.0 molar equivalents of the compound of Formula III at a reaction temperature from −50° C. to 100° C., preferably −25° C. to 50° C. to give a 3-thio substituent of Formula V. The reaction time depends on the kinds of the base and the compound of Formula III which are used, and the reaction temperature, but it is in the range of 10 minutes to 5 hours, usually 10 minutes to 2 hours. Preferred solvents in this reaction are N,N-dimethylformamide, N-N-dimethylacetamide, dimethyl sulfoxide, hexamethylphosphoramide, acetonitrile, tetrahydrofuran, dichloromethane, or a mixture thereof. The preferred base is an organic base such as diisopropylethylamine, triethylamine, N-N-dimethylaminopyridine, N-N-dimethylaniline and the like. The most preferred amount of the base is from 0.2 to 1.5 molar equivalents relative to the compound of Formula II.

Process (a'): The compound of Formula V can also be obtained by reaction of the compound of Formula II with the compound of Formula IV or the salt thereof. Examples of the salt of the compound of Formula IV are salts with metals such as silver, sodium, potassium, calcium, magnesium and the like. For example, in case that the silver salt is used as a salt of the compound of Formula IV, the salt is dissolved or suspended in a reaction-inert solvent, and sodium iodide or sodium isocyanate is added in 1.0 to 10 molar equivalents, preferably 4.0 to 7.0 molar equivalents relative to the salt, and the mixture is stirred at −20° to 50° C., preferably −5° to 30° C. for 10 minutes to one hour, preferably 10 to 30 minutes.

And then, to the reaction mixture is added 0.7 to 1.1 molar equivalents of the compound of Formula II in the form of a solid or a solution in the same solvent as described above, and the mixture is stirred. The reaction temperature is from −50° to 50° C., preferably from −30° to 20° C. The reaction time is from 5 minutes to 2 hours, preferably from 10 minutes to one hour. Examples of the preferred solvent used in this reaction are acetone, chloroform, dichloromethane, tetrahydrofuran, acetonitrile, diethyl ether, methanol, ethanol, benzene, N-N-dimethylformamide, N,N-dimethylacetamide, dimethyl sulfoxide, hexamethylphosphoramide, water, or a mixture thereof.

Meanwhile, in case that the compound of Formula IV is used in the form of a free thiol, the reaction can be carried out in the presence of a base under the same reaction conditions as described above.

Preferred bases used are organic bases such as diisopropylethylamine, triethylamine, N,N-dimethylaminopyridine, N,N-dimethylaniline and the like. The most preferred amount of the base is from 1.0 to 2.0 molar equivalents relative to the Compound II.

Process (b): The protecting group $R^4$ at the 7-position of the compound of Formula V obtained in the above process (a) or (a') can be eliminated by the method frequently used in the field of the $\beta$-lactam chemistry to give the compound of Formula VI. For example, the compound of Formula V wherein the protecting group $R^4$ is a phenoxyacetyl group, a phenylacetyl group or a benzoyl group, is stirred in a reaction solvent of dichloromethane or benzene in the presence of 1.5 to 2.0 molar equivalents of phosphorus pentachloride and 2.0 to 3.0 molar equivalents of pyridine at −40° C. to 30° C. for 30 minutes to 3 hours, thereafter a large excess amount of methanol is added at −50° C. to 20° C., and the mixture is stirred for 30 minutes to 2 hours and then treated with a large excess amount of water at −50° C. to 20° C. for 30 minutes to one hour to give the compound of Formula VI.

Furthermore, the compound of Formula V wherein the protecting group $R^4$ is a trityl group, is dissolved in a reaction-inert solvent (e.g., ethyl acetate), 1.0 to 1.5 molar equivalents of p-toluenesulfonic acid monohydrate is added under ice-cooling, and the mixture is stirred for 1 to 5 hours to give the compound of Formula VI in the form of p-toluenesulfonic acid salt. If necessary, the p-toluenesulfonic acid salt is treated with a base to give the compound of Formula VI in the form of the free base.

Process (c): In order to obtain the compound of Formula VIII from the compound of Formula VI, the compound of Formula VI is reacted with the 2-aminothiazoleacetic acid derivative of Formula VII in the presence of a condensing agent or reacted with a reactive derivative of the compound of Formula VII. Examples of the condensing agent are N,N'-dicyclohexylcarbodiimide, 1-ethoxy-carbonyl-2-ethoxy-1, 2-dihydroquinoline, N,N'-carbonyl-diimidazole, diphenylphosphoryl azide, Vilsmeier reagent and the like. Examples of the above reactive derivative of the compound of Formula VII are the acid halides (e.g., acid chloride and acid bromide), acid anhydride (e.g., symmetrical acid anhydrides of the compound of Formula VII, and mixed acid anhydrides with ethyl carbonate, diphenylphosphoric acid, methanesulfonic acid and the like), and activated esters (e.g., esters with p-nitrophenol, thiophenol, N-hydroxysuccinimide and the like). Referring to the acid chloride as the reactive derivative of the compound of Formula VII, first the compound of Formula VII is dissolved in a reaction-inert solvent, 1.0 to 1.1 molar equivalents of phosphorus pentachloride is added in the presence of a base at −30° C. to −10° C., and the mixture is stirred for 10 to 30 minutes to give an acid chloride of the compound of Formula VII. To the reaction mixture is added a solution of 0.7 to 1.0 molar equivalent of the compound of Formula VI in the same reaction-inert solvent as those mentioned above in the range of −30° C. to 0° C., and the mixture was stirred for 10 to 30 minutes to give the compound of Formula VIII. Preferred solvents used in this process are dichloromethane, chloroform, N-N-dimethylformamide, acetonitrile and the like. Preferred bases are pyridine, N,N-dimethylaniline, N,N-dimethylaminopyridine, triethylamine, diisopropylethylamine and the like. The amount of the base used is 4.0 to 5.5 molar equivalents relative to the compound of Formula VI.

Process (d): The protecting groups of the compound of Formula VIII are eliminated by the method frequently used in the field of the $\beta$-lactam chemistry, for example, by a method using trifluoroacetic acid-anisole to give the compound of Formula I. In this method, the compound of Formula VIII is reacted with a large excess amount of trifluoroacetic acid-anisole (volume ratio, 5 : 1) in a reaction-inert solvent or in the absence of solvent for 30 minutes to one hour, preferably at −5° C. to 25° C.

The compounds of Formula I of the present invention show not only strong antibacterial activity against various pathogenic bacteria but also high absorption by oral administration, therefore these compounds are useful as antibacterial agents for oral administration. For this purpose, they are administered orally in a conventional dosage form such as tablets, capsules, granules and the like which can be prepared according to usual pharmaceutical practices. In the above preparations are included conventional additives such as fillers, binding agents, disintegrators, vehicles, pH adjusting agents, solubilizers and the like.

Although the dosage of the compounds of the present invention depends on the age and conditions of the patient, the usual dosage is from 200 mg to 400 mg per person per day.

Subsequently, there were tested the minimal inhibitory concentration (MIC) of the compounds of the present invention against various bacteria and the concentration of the compound in blood after oral administration to rats, and the results are shown below.

Test 1

The antibacterial activities of the compounds of the present invention against various bacteria (inoculum size : $10^6$ cells/ml) were tested by the agar plate dilution method, and the results are shown in the following Table 1.

TABLE 1

| | MIC (μg/ml) | | | | |
| --- | --- | --- | --- | --- | --- |
| | Test compound | | | | |
| Bacteria | A | B | C | D | YY |
| Escherichia coli NIHJ JC-2 | 0.2 | 0.2 | 0.39 | 0.39 | 12.5 |
| Enterobactor cloacae IFO 13525 | 25 | 12.5 | 6.25 | 12.5 | >100 |
| Klebsiella pneumoniae T 25 | 0.39 | 0.39 | 0.39 | 0.39 | 100 |
| Pseudomonas aeruginosa NCTC 10490 | 25 | 3.13 | 12.5 | 6.25 | >100 |
| Serratia marcescens IID 618 | 1.56 | 0.39 | 0.39 | 0.39 | >100 |

(Note)
A: The compound obtained in Example 1
B: The compound obtained in Example 3
C: The compound obtained in Example 4
D: The compound obtained in Example 2
YY: Cefalexin (previously known compound)

Test 2

Male wister rats (7 weeks old) were administered orally with the test compound, and the change of the concentration of the compound in blood was measured. Dosage of the test compound: 50 mg/kg Quantitative method: Bioassy
test bacterium: Escherichia coli SC507)
The results are shown in Table 2.

TABLE 2

| | Concentration in blood (μg/ml) | | |
| --- | --- | --- | --- |
| | Test compound | | |
| Time | A | B | YY |
| 1.0 hour | 37.8 | 34.0 | 14.8 |
| 2.0 hours | 38.9 | 37.1 | 11.2 |
| 4.0 hours | 32.5 | 31.0 | 3.1 |

(Note)
A, B and YY are as defined above.

The present invention is illustrated in more detail by the following Examples but is not limited thereto.

EXAMPLE 1

(a) To a solution of 2.25 g (3 mM) of benzhydryl 7β-phenoxyacetamido-3-diphenylphosphoryloxy-3-cephem-4-carboxylate in 18 ml of N,N-dimethylformamide were added at $-10°$ C. a solution of 265 mg (3.3 mM) of 70% sodium hydrosulfide in 12 ml of N,N-dimethylformamide and 156 mg (1.2 mM) of diisopropylethylamine, and the mixture was stirred for 30 minutes. Subsequently, 504 mg (6 mM) of methyl propiolate was added at 0° C., and the mixture was stirred for 20 minutes. After the reaction, 150 ml of ethyl acetate was added, and the mixture was washed with a saturated aqueous sodium chloride solution (100 ml x 3) and dried over anhydrous magnesium sulfate. The solvent was evaporated, and the residue was purified by silica gel column chromatography (eluent; benzene : aectone=20 : 1 to 15 : 1) to give 1.17 g of benzhydryl 7β-phenoxyacetamido 3-[(Z)-2-methoxycarbonylvinylthio]-3-cephem-4-carboxylate.

NMR (CDCl$_3$) β (ppm); 3.48 (1H, d, J=18 Hz), 3.74 (3H, s), 3.78 (1H, d, J=18 Hz), 4.56 (2H, s), 5.07 (1H, d, J=5 Hz), 5.82 (1H, d, J=10 Hz), 5.94 (1H, dd, J=9 Hz, 5 Hz), 6.88 (1H, d, J=10 Hz), 6.90-7.10 (4H, m), 7.24=7.46 (13H, m)

IR $\nu^{KBr}_{max}$ cm$^{-1}$; 3280, 1780, 1686, 1490, 1360, 1215, 1160

(a') To a suspension of 241 mg (1.0 mM) of (Z)-2-methoxycarbonylvinylmercaptan silver salt in 10 ml of acetonitrile was added 900 mg (6.0 mM) of sodium iodide, and the mixture was stirred at room temperature for 30 minutes. To the reaction mixture was added at 0° C. a solution of 673 mg (0.9 mM) of benzhydryl 7β-phenoxyacetamido-3-diphenylphosphoryloxy-3-cephem-4-carboxylate in 10 ml of acetonitrile. After the mixture was stirred at the same temperature for 30 minutes, the insoluble solid was separated by filtration. To the filtrate was added 100 ml of ethyl acetate, and the mixture was washed with a saturated aqueous sodium chloride solution (50 ml×3) and dried over anhydrous magnesium sulfate. Subsequently, the solvent was evaporated, and the residue was purified by silica gel column chromatography (eluent; benzene : ethyl acetate =5 : 1) to give 490 mg of benzhydryl 7β-phenoxyacetamido-3-[(Z)-2-methoxycarbonylvinylthio]-3-cephem-4-carboxylate which was identical with the compound obtained in Example 1 (a).

(b) To a cooled ($-25°$ C.) solution of 480 mg (0.78 mM) of benzhydryl 7β-phenoxyacetamido-3-[(Z)-2-methoxycarbonylvinylthio]-3-cephem-4-carboxylate, obtained in the above (a) or (a'), in 10 ml of dry dichloromethane were added 185 mg (2.34 mM) of pyridine and 325 mg (1.56 mM) of phosphorus pentachloride, and the reaction temperature of the mixture was raised to 20° C. for a period of one hour, and then the mixture was stirred at the same temperature for one hour. To the cooled ($-50°$ C.) reaction mixture was added 5 ml of dry methanol, and the temperature of the mixture was raised to 0° C. over a one hour period. Upon continued cooling of the reaction mixture to $-40°$ C., 5 ml of water was added, and the reaction mixture was stirred under ice-cooling for 40 minutes. The reaction mixture was made weakly basic by addition of a saturated aqueous sodium bicarbonate solution and extracted with 50 ml of ethyl acetate. The extract was washed with 50 ml of a saturated aqueous sodium chloride solution and dried over anhydrous magnesium sulfate. The solvent was evaporated, and the residue was purified by silica gel column chromatography (eluent; ethyl acetate : n-hexane=1 : 1 to 2 : 1) to give 198 mg of benzhydryl 7β-amino-3-[(Z)-2-methoxy-carbonylvinylthio]-3-cephem-4-carboxylate.

(c) To a cooled ($-10°$ C.) solution of 310 mg (0.47 mM) of α-(2-tritylaminothiazole-4-yl)-α-[(Z)-benzhydryloxycarbonylmethoxyimino] acetic acid in 7 ml of dry dichloromethane were added 188 mg (2.35 mm, of pyridine and 99 mg (0.47 mM) of phosphorus pentachloride, and the reaction mixture was stirred for 20 minutes. Subsequently, a solution of the 7-amino derivative (198 mg, 0.41 mM) obtained in Example 1 (b) in dry dichloromethane (2 ml) was added at the temperature, and the reaction mixture was stirred for 20 minutes. After the reaction, 50 ml of ethyl acetate was added, and the reaction mixture was washed with 30 ml of 0.5% hydrochloric acid and 30 ml of a saturated aqueous sodium chloride solution, successively, and dried over anhydrous magnesium sulfate. The solvent was evaporated, and the residue was purified by silica gel column chromatography (eluent; benzene : acetone =20 : 1 to 15 : 1) to give 360 mg of benzhydryl 7β-{α-(2tritylaminothiazole4yl)-α-(Z)-benzhydryloxycarbonylmethoxyimino] acetamido}-3-[(Z)-2-methoxycarbonylvinylthio]-3-cephem-4-carboxylate.

NMR (CDCl$_3$) δ (ppm); 3.22 (1H, d, J=17 Hz), 3.61 (1H, d, J=17 Hz), 3.77 (3H, s), 4.89 (1H, d, J=17 Hz), 5.04 (1H, d, J=5 Hz), 5.07 (1H, d, J=17 Hz), 5.81 (1H, d, J=11 Hz), 5.95 (1H, dd, J=9 Hz, J-5 Hz), 6.80 (1H, s), 6.81 (1H, d, J=11 Hz), 6.97 (1H, s), 7.02 (2H, s), 7.23-7.48 (35H, m), 8.11 (1H, d, J=9 Hz)

(d) To a mixture of trifluoroacetic acid (5 ml) and anisole (1 ml) was added under ice-cooling 360 mg (0.32 mM) of benzyhydryl 7β-{α-(2-tritylaminothiazole-4-yl)-α-[(Z)benzhydryloxycarbonylmethoxyimino]acetamido}-3-[(Z)-2methoxycarbonylvinylthio]-3-cephem-4-carboxylate, and the reaction mixture was stirred for 40 minutes. The reaction mixture was slowly added dropwise to a mixture of diethyl ether and n-hexane (1 : 2, 40 ml), and the crystals which formed were collected by filtration to give 230 mg of the desired trifluoroacetate. Then, the crystals and 82 mg (0.98 mM) of sodium bicarbonate were dissolved in 5 ml of water, thereafter, the solution was treated by Sephadox LH-20 column chromatography (eluent; water) to give 180 mg of 7β-{α-(2-aminothiazole-4-yl)-β-[(Z)-carboxymethoxyimino]acetamido)}-3[(Z)-2-methoxycarbonylvinylthio]-3-cephem-4-carboxylic acid sodium salt.

NMR (D$_2$) δ (ppm); 3.58 (1H, d, J=17 Hz), 3.77 (3H, s), 3.98 (1H, d, J=17 Hz), 4.60 (2H, s), 5.32 (1H, d, J=5

Hz), 5.89 (1H, d, J=5 Hz), 6.06 (1H, d, J=11 Hz), 7.08 (1H, s), 7.35 (1H, d, J=11 Hz)

IR $\nu^{KBr}_{max}$ cm$^{-1}$; 3380, 1760, 1675, 1600, 1350, 1200

EXAMPLE 2

(a) To a cooled (−10° C.) solution of 1.5 g (2 mM) of benzhydryl 7β-phenoxyacetamido-3-diphenylphosphoryloxy-3-cephem-4-carboxylate in 12 ml of N,N-dimethylformamide were added a solution of 177 mg (2.2 mM) of 70% sodium hydrosulfide in 8 ml of N,N-dimethylformamide and 310 mg (2.4 mM) of diisopropylethylamine, and the reaction mixture was stirred for 30 minutes. Subsequently, 330 mg (3 mM) of allyl propiolate was added at the same temperature, and the reaction mixture was stirred for 40 minutes. After the reaction, 50 ml of 0.5% hydrochloric acid was added, the mixture was extracted with 100 ml of ethyl acetate, and the extract was washed with a saturated aqueous sodium chloride solution (100 ml×2) and dried over anhydrous magnesium sulfate. The solvent was evaporated, and the residue was purified by silica gel column chromatography (eluent; ethyl acetate : n-hexane=2 : 3 to 1 : 1) to give 820 mg of benzhydryl 7β-phenoxyacetamido-3-[(Z)-2allyloxycarbonylvinylthio]-3-cephem-4-carboxylate.

NMR (CDCl$_3$) β (ppm; 3.49 (1H, d, J=17 Hz), 3.80 (1H, d, J=17 Hz), 4.58 (2H, s), 4.66 (2H, m), 5.09 (1H, d, J=5 Hz), 5.23–5.43 (2H, m), 5.85 (1H, d, J=11 Hz), 5.87–6.07 (2H, m), 6.91 (1H, d, J=11 Hz), 6.90–7.11 (4H, m), 7.25-7.76 (13H, m)

IR $\nu^{KBr}_{max}$cm$^{-1}$; 3280, 3030, 1780, 1685, 1490, 1370, 1210, 1155

(b) To a cooled (−25°C.) solution of 750 mg (1.17 mM) of benzhydryl 7β-phenoxyacetamido-3-[(Z)-2-allyloxycarbonylvinylthio]-3-cephem-4-carboxylate, obtained in the above (a), in 14 ml of dry dichloromethane were added 278 mg (3.51 mm of pyridine and 487 mg (2.34 mm of phosphorus pentachloride, and the reaction temperature was raised to 20° C. for a period of one hour, and then the reaction mixture was stirred at the same temperature for one hour. To the cooled (−50° C.) reaction mixture was added 7 ml of dry methanol, and the temperature was raised to 0°C. for a period of one hour. Upon continued cooing of the reaction mixture to −40°C., 5 ml of water was added, and the reaction mixture was stirred under ice-cooling for 40 minutes. The reaction mixture was made weakly basic by addition of a saturated aqueous sodium bicarbonate solution and extracted with 50 ml of ethyl acetate. The extract was washed with 50 ml of a saturated aqueous sodium chloride solution and then dried over anhydrous magnesium sulfate. The solvent was evaporated and the residue was purified by silica gel column chromatography (eluent; ethyl acetate : n-hexane =1 : 1 to 2 : 1) to give 300 mg of benyhydryl 7β-amino-3-[(Z)-2-allyloxycarbonylvinylthio]-3-cephem-4-carboxylate.

NMR (CDCl$_3$) β(ppm); 1.74 (2H, bs), 3.47 (1H, d, J=17 Hz), 3.80 (1H, d, J=17 Hz), 4.65 (2H, m), 4.79 (1H, d, J=5 Hz), 4.99 (1H, d, J=5 Hz), 5.23–5.44 (2 H, m), 5.82 (1H, d, J=11 Hz), 5.84–6.08 (1H, m), 6.92 (1H, d, J=11 Hz), 7.02 (1H, s), 7.24–7.44 (10 H, m)

(c) To a cooled (−10° C.) solution of 414 mg (0.63 mM) of α-(2-tritylaminothiazole-4-yl)-α-[(Z)-benzhydryloxycarbonylmethoxyimino]acetic acid in 11 ml of dry dichloromethane were added 251 mg (3.15 mM) of pyridine and 132 mg (0.63 mM) of phosphorus pentachloride, and the reaction mixture was stirred for 20 minutes. Subsequently, a solution of the 7-amino derivative (280 mg, 0.55 mM) obtained in the above (b) in dry dichloromethane (2 ml) was added, and the reaction mixture was stirred at the same temperature for 20 minutes. After the reaction, 30 ml of 0.5% hydrochloric acid was added, and the mixture was extracted with 50 ml of ethyl acetate. The extract was washed with 30 ml of a saturated aqueous sodium chloride solution and dried over anhydrous magnesium sulfate. The solvent was evaporated and the residue was purified by silica gel column chromatography (eluent; ethyl acetate : n-hexane =2 : 3 to 1 : 1) to give 295 mg of benzhydryl 7β-{α-(2-tritylaminothiazole-4-yl)-α-[(Z)-benhydryloxycarbonylmethoxyimino]acetamido}-3-[(Z)-2-allyloxycarbonylvinylthio]-3-cephem-4-carboxylate.

NMR (CDCl$_3$) δ(ppm); 3.22 (1H, d, J=16 Hz), 3.61 (1H, d, J=16 Hz), 4.68 (2H, m), 4.89 (1H, d, J=17 Hz), 5.04 (1H, d, J=5 Hz), 5.06 (1H, d, J=17 Hz), 5.24–5.45 (2H, m) 5.83 (1H, d, J=11 Hz), 5.88–6.09 (2H, m), 6.80 (1H, s), 6.83 (1H, d, J=11 Hz), 6.96 (1H, s), 7.01 (2H, bs), 7.22–7.48 (35H, m), 8.11 (1H, d, J=9 Hz)

IR $\nu^{KBr}_{max}$cm$^{-1}$; 3360, 3030, 1785, 1685, 1510, 1370, 1210

(d) To a mixture of trifluoroacetic acid (3.5 ml) and anisole (0.7 ml) was added under ice-cooling benzhydryl 7β-{α-(2-tritylaminothiazole-4-yl)-α-[(Z)benzhydryloxycarbonylmethoxyimino]acetamido}-3-[(Z)-2allyloxycarbonylvinylthiol]-3-cephem-4-carboxylate (280 mg, 0.24 mM), and the reaction mixture was stirred for 40 minutes. The reaction mixture was added slowly dropwise to a mixture of diethyl ether and n-hexane (1 : 2, 30 ml), and the crystals which formed were collected by filtration to give 190 mg of the desired trifluoroacetate. Subsequently, the crystals and 62 mg (0.72 mM) of sodium bicarbonate were dissolved in 4 ml of water, and the solution was treated by Sephadex LH-20 column chromatography (eluent; water) to give 170 mg of 7β-{α-(2-aminothiazole-4-yl)-α-[(Z)-carboxymethoxyimino]acetamido}-3- [(Z)-2-allyloxycarbonylvinylthio]-3-cephem-4-carboxylic acid sodium salt.

NMR (D$_2$O ) δ (ppm); 3.60 (1H, d, J=17 Hz), 3.99 (1H, d, J=17 Hz), 4.60 (2H, s), 4.70 (2H, m), 5.28–5.46 (2H, m), 5.33 (1H, d, J=5 Hz), 5.90 (1H, d, J-5 Hz), 5.91–6.07 (1H, m), 6.09 (1H, d, J=11 Hz), 7.08 (1H, s), 7.39 (1H, d, J-11 Hz)

IR $\nu^{KBr}_{max}$cm$^{-1}$; 3380, 1760, 1600, 1375, 1345, 1200, 1165

Following the procedure of Example 1 or 2, using the corresponding compounds there were obtained the following compounds indicated in Table 3.

TABLE 3

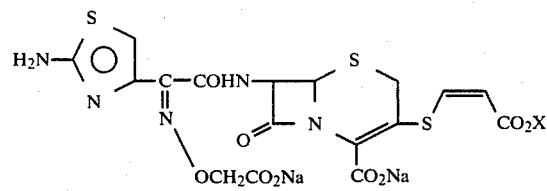

| Example number | X | NMR (D$_2$O) δ(ppm) | IR $\nu^{KBr}_{max}$ cm$^{-1}$ |
|---|---|---|---|
| 3 | —CH$_2$CH$_3$ | 1.30 (3H, t, J = 7 Hz) | 3340 |
|  |  | 3.58 (1H, d, J = 17 Hz) | 1760 |
|  |  | 3.98 (1H, d, J = 17 Hz) | 1590 |
|  |  | 4.25 (2H, q, J = 7 Hz) | 1380 |
|  |  | 4.60 (2H, s) | 1345 |
|  |  | 5.33 (1H, d, J = 5 Hz) | 1165 |
|  |  | 5.90 (1H, d, J = 5 Hz) |  |
|  |  | 6.05 (1H, d, J = 11 Hz) |  |
|  |  | 7.08 (1H, s) |  |

TABLE 3-continued

[Structure: H2N-thiazole-C(=N-OCH2CO2Na)-COHN-cephem-S-CH=CH-CO2X with CO2Na]

| Example number | X | NMR (D₂O) δ(ppm) | IR $\nu_{max}^{KBr}$ cm$^{-1}$ |
|---|---|---|---|
| | | 7.35 (1H, d, J = 11 Hz) | |
| 4 | $-CH(CH_3)_2$ | 1.28 (6H, d, J = 7 Hz) | 3360 |
| | | 3.58 (1H, d, J = 18 Hz) | 1760 |
| | | 3.97 (1H, d, J = 18 Hz) | 1600 |
| | | 4.60 (2H, s) | 1370 |
| | | 5.06 (1H, m) | 1170 |
| | | 5.31 (1H, d, J = 5 Hz) | |
| | | 5.88 (1H, d, J = 5 Hz) | |
| | | 6.00 (1H, d, J = 10 Hz) | |
| | | 7.07 (1H, s) | |
| | | 7.32 (1H, d, J = 10 Hz) | |
| 5 | cyclohexyl | 1.20–1.96 (10H, m) | 3370 |
| | | 3.58 (1H, d, J = 17 Hz) | 2920 |
| | | 3.97 (1H, d, J = 17 Hz) | 1760 |
| | | 4.60 (2H, s) | 1600 |
| | | 4.78–4.90 (1H, m) | 1350 |
| | | 5.32 (1H, d, J = 5 Hz) | 1200 |
| | | 5.88 (1H, d, J = 5 Hz) | 1170 |
| | | 6.02 (1H, d, J = 11 Hz) | |
| | | 7.08 (1H, s) | |
| | | 7.34 (1H, d, J = 11 Hz) | |
| 6 | $CH_2$–phenyl | 3.52 (1H, d, J = 17 Hz) | 3360 |
| | | 3.92 (1H, d, J = 17 Hz) | 1760 |
| | | 4.60 (2H, s) | 1595 |
| | | 5.23 (2H, s) | 1380 |
| | | 5.29 (1H, d, J = 5 Hz) | 1350 |
| | | 5.87 (1H, d, J = 5 Hz) | 1205 |
| | | 6.50 (1H, d, J = 11 Hz) | 1160 |
| | | 7.05 (1H, s) | |
| | | 7.35 (1H, d, J = 11 Hz) | |
| | | 7.46 (5H, bs) | |

TABLE 3-continued

[Structure same as above]

| Example number | X | NMR (D₂O) δ(ppm) | IR $\nu_{max}^{KBr}$ cm$^{-1}$ |
|---|---|---|---|
| 7 | —Na | 3.59 (1H, d, J = 17 Hz) | 3340 |
| | | 3.96 (1H, d, J = 17 Hz) | 1755 |
| | | 4.60 (2H, s) | 1585 |
| | | 5.31 (1H, d, J = 5 Hz) | 1385 |
| | | 5.88 (1H, d, J = 5 Hz) | 1295 |
| | | 5.96 (1H, d, J = 10 Hz) | |
| | | 6.88 (1H, d, J = 10 Hz) | |
| | | 7.08 (1H, s) | |

What is claimed is:

1. Cephalosporin derivatives represented by the formula

[Structure: aminothiazole-C(=N-OCH2CO2H)-CONH- linked to cephem-S-CH=CH-CO2X with CO2H]

wherein X represents a hydrogen atom, a lower alkyl group having 1 to 4 carbon atoms, an allyl group, a cycloalkyl group having 5 or 6 carbon atoms or a benzyl group, and pharmaceutically acceptable, non-toxic salts thereof.

2. A cephalosporin derivative according to claim 1 wherein X is a methyl group.

3. A cephalosporin derivative according to claim 1 wherein X is an ethyl group.

4. A cephalosporin derivative according to claim 1 wherein X is an isopropyl group.

5. A cephalosporin derivative according to claim 1 wherein X is an allyl group.

* * * * *

UNITED STATES PATENT AND TRADEMARK OFFICE
CERTIFICATE OF CORRECTION

PATENT NO. : 4,699,981
DATED : October 13, 1987
INVENTOR(S) : WANTANABE et al

It is certified that error appears in the above—identified patent and that said Letters Patent is hereby corrected as shown below:

Column 7, line 21, "265" should read --264--.

Column 8, line 24, "mm" should read --mM--, line 29, after "the" insert --same--.

Column 9, line 38, delete "mm" and insert --mM)--.

Signed and Sealed this

Nineteenth Day of April, 1988

Attest:

DONALD J. QUIGG

Attesting Officer     Commissioner of Patents and Trademarks